US011412956B2

(12) United States Patent
Soltani et al.

(10) Patent No.: US 11,412,956 B2
(45) Date of Patent: Aug. 16, 2022

(54) METHODS FOR COMPUTING A REAL-TIME STEP LENGTH AND SPEED OF A RUNNING OR WALKING INDIVIDUAL

(71) Applicant: The Swatch Group Research and Development Ltd, Marin (CH)

(72) Inventors: Abolfazl Soltani, Lausanne (CH); Hooman Dejnabadi, Orbe (CH); Kamiar Aminian, La Tour-de-Peilz (CH)

(73) Assignee: The Swatch Group Research and Development Ltd, Marin (CH)

( * ) Notice: Subject to any disclaimer, the term of this patent is extended or adjusted under 35 U.S.C. 154(b) by 587 days.

(21) Appl. No.: 16/428,001

(22) Filed: May 31, 2019

(65) Prior Publication Data

US 2020/0000374 A1 Jan. 2, 2020

(30) Foreign Application Priority Data

Jun. 27, 2018 (EP) .................................... 18180129

(51) Int. Cl.
*A61B 5/11* (2006.01)
*A61B 5/00* (2006.01)
*G06F 3/01* (2006.01)
*G06F 17/16* (2006.01)

(52) U.S. Cl.
CPC .............. *A61B 5/112* (2013.01); *A61B 5/681* (2013.01); *G06F 3/011* (2013.01); *G06F 3/017* (2013.01); *G06F 17/16* (2013.01); *A61B 2562/0219* (2013.01); *A61B 2562/0247* (2013.01)

(58) Field of Classification Search
CPC ........................................................ A61B 5/112
See application file for complete search history.

(56) References Cited

U.S. PATENT DOCUMENTS

| | | | |
|---|---|---|---|
| 2004/0064286 | A1 | 4/2004 | Levi et al. |
| 2005/0033200 | A1 | 2/2005 | Soehren et al. |
| 2009/0007661 | A1* | 1/2009 | Nasiri ............... G01C 19/5769 73/504.03 |
| 2012/0083705 | A1 | 4/2012 | Yuen et al. |
| 2012/0083714 | A1 | 4/2012 | Yuen et al. |
| 2012/0083715 | A1 | 4/2012 | Yuen et al. |

(Continued)

FOREIGN PATENT DOCUMENTS

| | | |
|---|---|---|
| CA | 2 382 999 A1 | 10/2002 |
| CN | 202904027 U | 4/2013 |

(Continued)

OTHER PUBLICATIONS

Japanese Office Action dated Jun. 30, 2020 in Patent Application No. 2019-105042 (with English translation), 6 pages.

(Continued)

*Primary Examiner* — Hyun D Park
(74) *Attorney, Agent, or Firm* — Oblon, McClelland, Maier & Neustadt, L.L.P.

(57) ABSTRACT

A method for calculating an estimation of the speed $\hat{V}[n']$ of an individual walking along a path, over a time window including: computing a step length $\widehat{SL}[n']$ of the individual, calculating the speed $\hat{V}[n']$ using the following formula: $\hat{V}[n']=\widehat{SL}[n']\times\widehat{cad}[n']$.

12 Claims, 5 Drawing Sheets

(56) References Cited

U.S. PATENT DOCUMENTS

| | | |
|---|---|---|
| 2012/0083716 A1 | 4/2012 | Yuen et al. |
| 2012/0084053 A1 | 4/2012 | Yuen et al. |
| 2012/0084054 A1 | 4/2012 | Yuen et al. |
| 2012/0226471 A1 | 9/2012 | Yuen et al. |
| 2012/0226472 A1 | 9/2012 | Yuen et al. |
| 2013/0073254 A1 | 3/2013 | Yuen et al. |
| 2013/0073255 A1 | 3/2013 | Yuen et al. |
| 2013/0080113 A1 | 3/2013 | Yuen et al. |
| 2013/0096843 A1 | 4/2013 | Yuen et al. |
| 2013/0151196 A1 | 6/2013 | Yuen et al. |
| 2013/0158369 A1 | 6/2013 | Yuen et al. |
| 2013/0268236 A1 | 10/2013 | Yuen et al. |
| 2013/0297220 A1 | 11/2013 | Yuen et al. |
| 2014/0067278 A1 | 3/2014 | Yuen et al. |
| 2014/0309964 A1 | 10/2014 | Li et al. |
| 2014/0343867 A1 | 11/2014 | Yuen et al. |
| 2015/0134268 A1 | 5/2015 | Yuen et al. |
| 2016/0166156 A1 | 6/2016 | Yuen et al. |
| 2017/0273637 A1* | 9/2017 | Sugiyama ............... A61B 5/11 |
| 2017/0292968 A1 | 10/2017 | Shiina |
| 2017/0347239 A1 | 11/2017 | MacGougan et al. |
| 2018/0055376 A1 | 3/2018 | Yuen et al. |
| 2018/0146907 A1* | 5/2018 | Nishiyama ......... A63B 71/0622 |
| 2018/0156920 A1 | 6/2018 | Diggelen et al. |

FOREIGN PATENT DOCUMENTS

| | | |
|---|---|---|
| CN | 104729524 A | 6/2015 |
| CN | 105122006 A | 12/2015 |
| EP | 3 196 658 A1 | 7/2017 |
| JP | 2007-93433 A | 4/2007 |
| KR | 10-2014-0090071 A | 7/2014 |
| WO | WO 2012/045483 A1 | 4/2012 |

OTHER PUBLICATIONS

European Search Report dated Dec. 6, 2018 in European Application 18180129.1 filed on Jun. 27, 2018.

Fasel, B., et al., "A wrist sensor and algorithm to determine instantaneous walking cadence and speed in daily life walking", Medical and Biological Engineering and Computing, vol. 55, No. 10, Feb. 14, 2017, pp. 1773-1785.

Combined Chinese Office Action and Search Report dated Nov. 26, 2021 in Chinese Patent Application No. 201910547224.7 (with English translation), 10 pages.

* cited by examiner

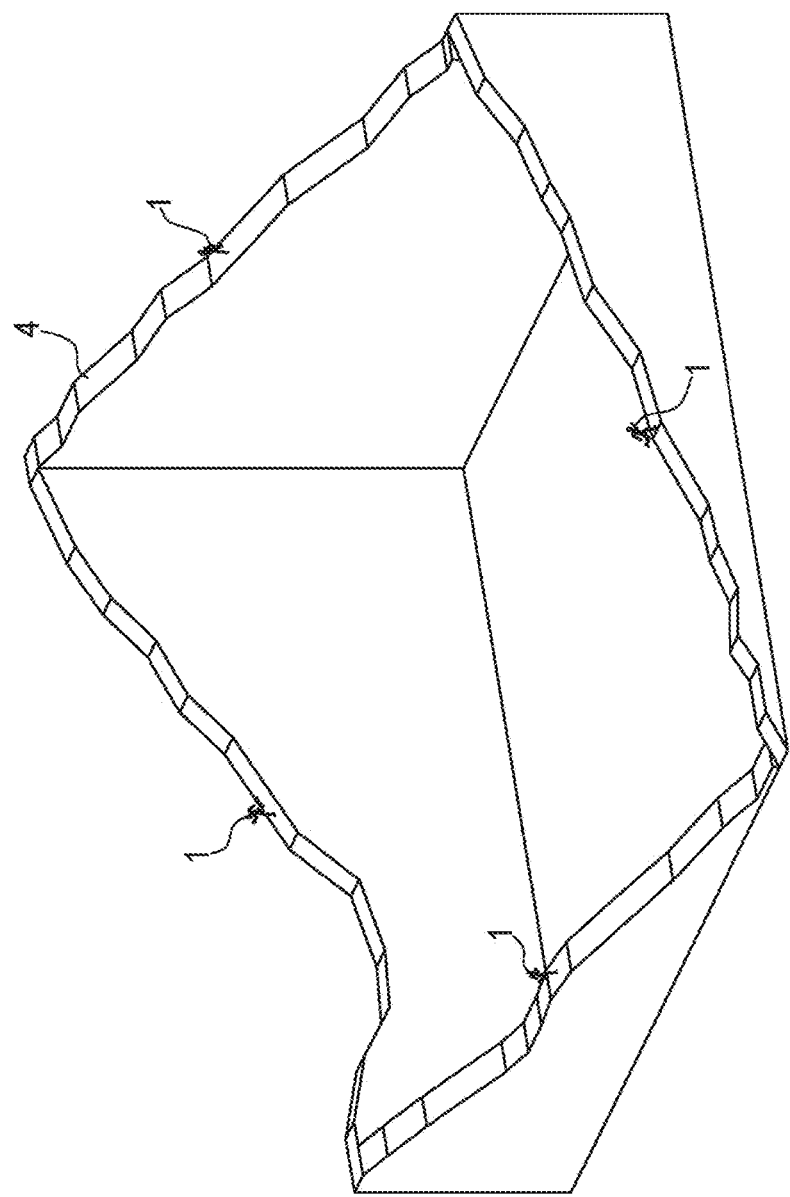
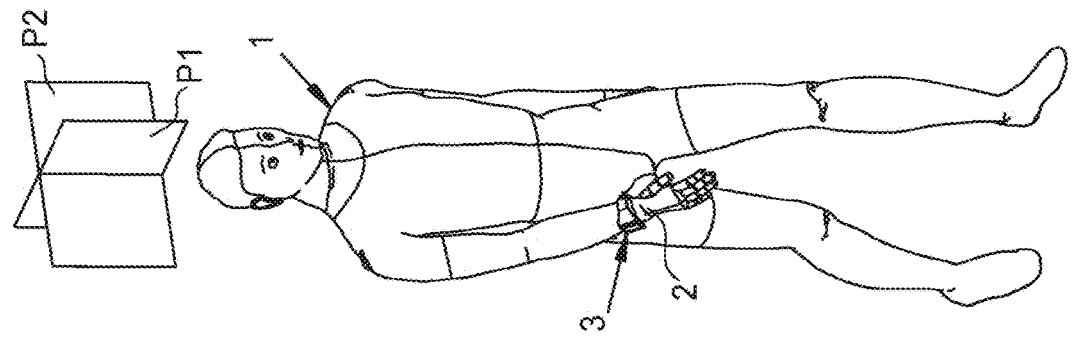

METHODS FOR COMPUTING A REAL-TIME STEP LENGTH AND SPEED OF A RUNNING OR WALKING INDIVIDUAL

CROSS-REFERENCE TO RELATED APPLICATION

This application claims priority to European Patent Application No. 18180129.1 filed on Jun. 27, 2018, the entire disclosure of which is hereby incorporated herein by reference.

FIELD OF THE INVENTION

The invention relates to methods for computing a real-time estimation of the step length and the speed of a walking or running individual.

BACKGROUND OF THE INVENTION

Gait speed and step length are important parameters to characterize an individual's daily activities. In sport applications for instance, speed may be used to evaluate athletes and to design personalized training sessions, with a view to improve performance and decrease the risk of injury. In clinical applications, speed is used to evaluate the individual's health, thereby helping doctors diagnose, predict and prevent many diseases such as diabetes, overweight or cardiovascular pathologies.

Global Navigation Satellite System (GNSS) is a basic system widely used to measure an individual's gait speed. GNSS is accurate, and many wearable devices have been designed to embed a GNSS transponder, the measurements of which may be used to compute the individual's gait speed even in real-life conditions. However, there are locations where the GNSS signal is weak or might even be lost due to the lack of satellite coverage, such as indoors, tunnels, near high buildings, narrow valleys. In addition, a GNSS transponder is very power consuming, whereby it is preferable to use it sporadically instead of continuously.

Inertial sensors-based systems are yet another way to measure an individual's gait speed in daily life. While most inertial sensors are used attached to lower limb of the individual's body (such as feet, shanks, thighs), few are used attached to upper limbs (such as trunk and waist).

It is also known to use multiple sensors attached to different parts of the individual's body, the measurements of which are combined to enhance performance of gait speed estimation.

Inertial sensors-based systems estimate gait speed through multiplying gait cadence (i.e. the number of steps per time unit) by step length. Those systems usually compute the cadence by sensing certain moments (e.g. hill-strike, toe-off, mid-swing) during the different gait phases.

In usual inertial sensors-based systems, a step length is computed through geometric modelling of the individual's gait (e.g. based on inverse pendulum movement), double integration of acceleration, or an abstract modelling of the gait based on machine learning.

One main advantage of the inertial-based systems is their possible usage in daily life conditions. Another advantage of the inertial systems is their acceptable accuracy. One main drawback, however, is that those systems need sensor calibration at the beginning of each measurement phase, which requires expertise from the user to wear them on the body. Another drawback is that the location of the sensors on the user's body are often regarded as an inconvenient, especially when a plurality of sensors are required. This might explain their commercial failure.

Only recently were methods introduced to estimate the gait speed of an individual based on wrist-worn inertial sensors.

Most known methods use an abstract modelling, which extracts several features from raw data and then build a regression model to estimate speed. Basic features for the wrist-based speed estimation are energy of the signal, cadence, mean crossing rate, and statistical features like mean, standard deviation, mode, and median of acceleration signal, see e.g. B. Fasel et al., "A wrist sensor and algorithm to determine instantaneous walking cadence and speed in daily life walking," Med. Biol. Eng. Comput., vol. 55, pp. 1773-1785, 2017. Fasel also proposes intensity of the movement as a feature, which is a multiplication of mean and standard deviation of the wrist acceleration. Fasel yet also proposed the slope of the path (based on pressure sensor) as a feature for speed estimation.

However, even the best methods (including Fasel's) only exploit a little piece of useful information from the physics of hand and body movements. Moreover, the existing methods rely upon a general speed model, which results from an effort to standardize the individual to an average of a large population of humans. While efforts were made to somewhat adapt the general speed model with age, sex, height, and weight parameters, the model remains a standard ignorant of the strategy that each individual might exploit to manage his/her gait speed during physical effort.

SUMMARY OF THE INVENTION

It is an object of the present invention to propose a method for accurate and real-time estimation of the step length of a walking or running individual.

Another object of the invention is to propose a personalized method capable of learning the individual's gait and automatically adapt to his/her activity behaviour.

Another object of the invention is to propose a method that might be implemented within a wrist-wearable device, providing easy-to-use measurements for long-term monitoring of physical activities.

Another object of the invention is to propose a low-consumption computing method to increase autonomy of the wrist-wearable device.

It is therefore proposed, in a first aspect a method for computing an estimation of the step length of an individual over a time window, according to claim 1.

It is proposed, in a second aspect, a method for calculating an estimation of the speed of the individual over the time window, according to claim 10.

It is proposed, in a third aspect, a computer program product implemented on a readable memory connected to a calculation unit, said computer program including the instructions for conducting the method for computing the step length and/or the method for computing the speed as disclosed hereinbefore.

It is proposed, in a fourth aspect, a wrist-wearable device including a calculation unit and a readable memory connected to the readable memory, said readable memory being implemented with the computer program mentioned here above.

BRIEF DESCRIPTION OF THE DRAWINGS

The above and further objects and advantages of the invention will become apparent from the detailed description of preferred embodiments, considered in conjunction with the accompanying drawings.

FIG. 1 is a perspective view of an individual having a wrist-wearable device attached to the wrist.

FIG. 2 is a schematic perspective view of a path followed by an individual during a walking (or running) session.

DETAILED DESCRIPTION

Figure 3:
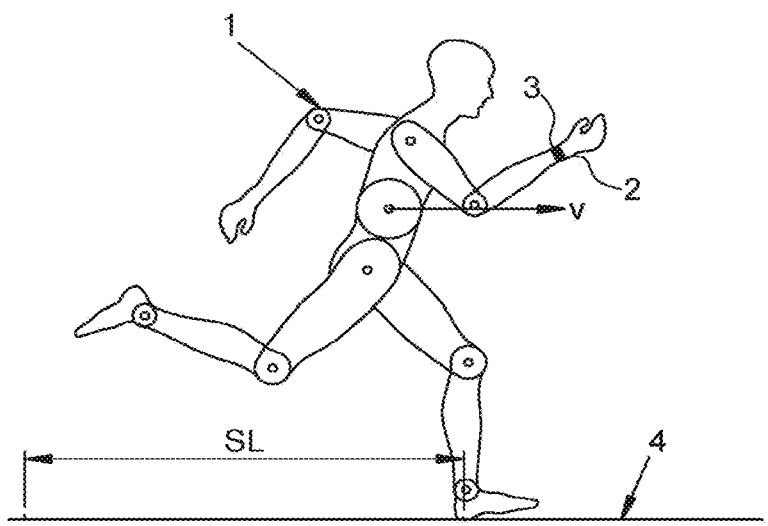
FIG. 3, FIG. 4 and FIG. 5 are schematic side views of an individual running on a path with no slope (FIG. 3), positive slope (FIG. 4) and negative slope (FIG. 4).

On FIG. 1 is schematically drawn an individual on foot 1. The individual 1 is supposed to be healthy and have all his/her members, including legs and arms, the arms having wrists 2. The individual 1 defines a vertical sagittal plane P1 (which is the global symmetry plane of the individual 1) and a vertical front plane P2, which is perpendicular to the sagittal plane P1. As depicted on FIG. 1, a wrist-wearable device or "smartwatch" 3 is attached to at least one of the individual's wrists, here to the right wrist 2.

The smartwatch 3 is configured to monitor activity and infer various parameters of the individual 1 while he/she is moving on foot (i.e. either running or walking) on a path 4, the variations of altitude of which are voluntarily exaggerated on FIG. 2.

Figure 4:
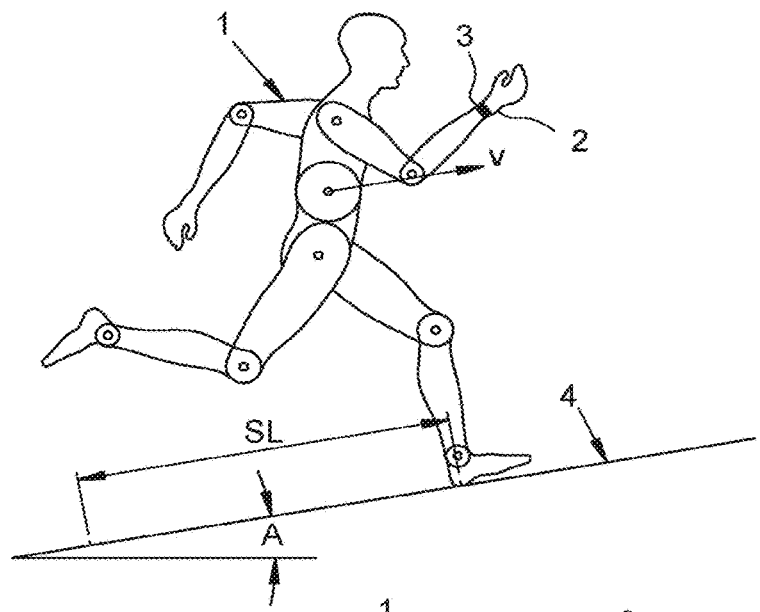
Figure 5:
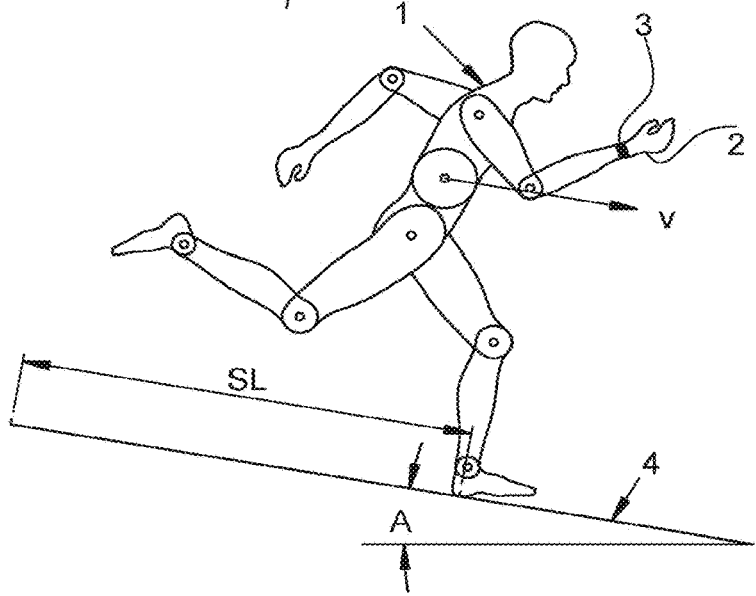
Figure 6:
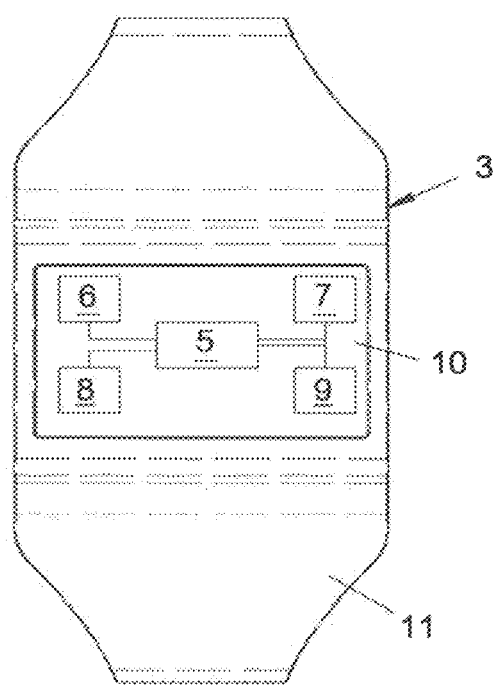
FIG. 6 is a wrist-wearable device embedding a system for computing a real-time estimation of the step length and speed of a walking or running individual.
Figure 7:
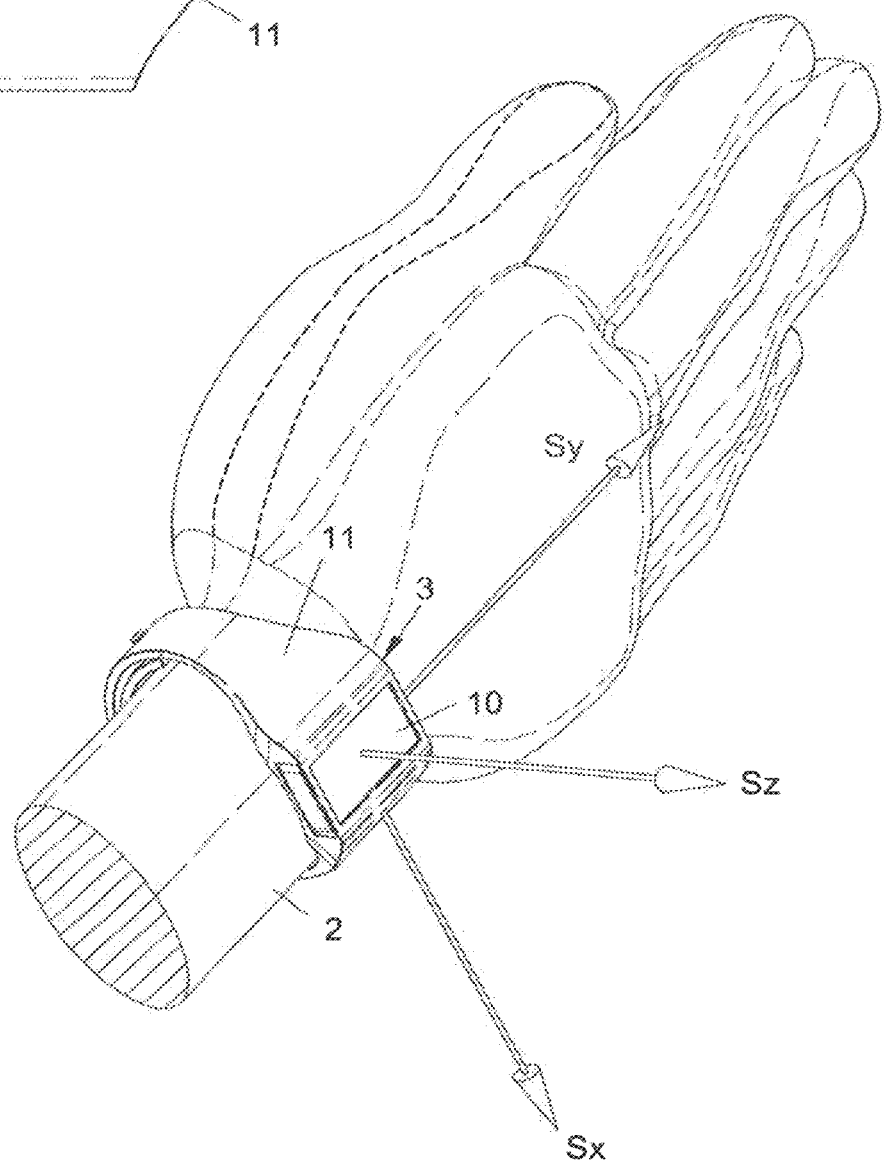
FIG. 7 is a perspective view showing an individual's hand in movement, with the wrist-wearable device of FIG. 6 attached to it.
Figure 8:
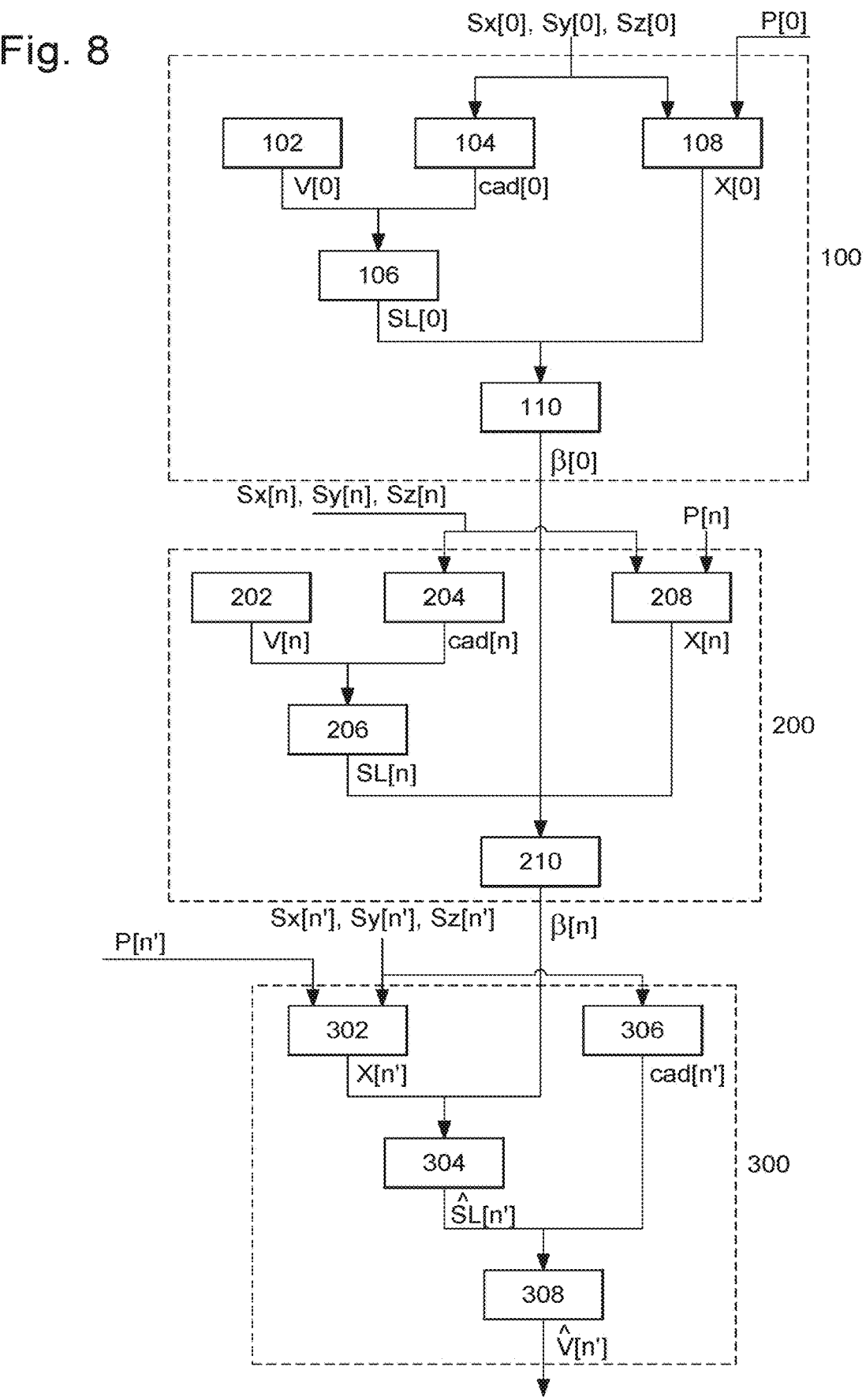
FIG. 8 is a diagram summarizing different phases and steps of a method for computing a real-time estimation of the step length and speed of a walking or running individual.

Indeed, while some portions of the path 4 may be flat (as shown on FIG. 3), other portions may be inclined and have a slope A which, from the individual's point of view, may be positive (FIG. 4) or negative (FIG. 5).

The individual 1 is moving:
at a gait speed noted V (expressed in m·s$^{-1}$),
at a cadence noted cad (expressed in s$^{-1}$ or Hz),
with a step length noted SL (expressed in m).

The smartwatch 3 is equipped with:
a calculation unit 5,
a readable memory 6 connected to the calculation unit 5,
an accelerometer 7, a barometer 8 and a GNSS transponder 9 all connected to the calculation unit 5.

The calculation unit 5, readable memory 6, accelerometer 7, barometer 8 and GNSS transponder 9 are embedded in a casing 10 attached to the wrist 2 by means of a strap or bracelet 11.

The readable memory 6 is implemented with a computer program including instructions for conducting a method for computing at least an estimation of the step length over a time window n, noted $\widehat{SL}[an]$, of the individual 1 along the path 4, and preferably also an estimation of his/her gait speed over time window n, noted $\hat{V}[n]$.

The computed step length $\widehat{SL}[n]$ and computed speed $\hat{V}[n]$ are linked to one another by the following equation:

$$\hat{V}[n] = \widehat{cad}[n] \times \widehat{SL}[n],$$

where $\widehat{cad}[n]$ is an estimated cadence of the individual 1 over time window n.

It should be noted that n is an integer where $n \in [1, \ldots N]$, N being an integer higher than 1. $[1, \ldots N]$ represents a time range starting from a first time window n=1 corresponding to the beginning of the computing to a last time window n=N corresponding to the end of the computing. In a preferred embodiment, time windows are 7-second long with 6-second overlap.

The method uses instant acceleration measures provided by the accelerometer 7 and instant atmospheric pressure measures provided by the barometer 8.

The accelerometer 7 is configured to deliver acceleration measures along three perpendicular axes, namely:
a first acceleration along an X axis perpendicular to the arm of the individual 1 and parallel to his/her sagittal plane P1,
a second acceleration along a Y axis parallel to the arm of the individual 1 and parallel to his/her sagittal plane P1,
a third acceleration along a Z axis perpendicular to the arm of the individual 1 and parallel to his/her front plane P2.

For each axis X, Y, Z, z acceleration samples are taken per window, z being an integer higher than 1:
$S_x^i[n]$ is the i-th acceleration sample along the X axis, delivered by the accelerometer (7) along time window n,
$S_y^i[n]$ is the i-th acceleration sample along the Y axis, delivered by the accelerometer (7) along time window n,
$S_z^i[n]$ is the i-th acceleration sample along the Z axis, delivered by the accelerometer (7) along time window n.

For convenience, in the rest of the description, the following notations will be used:

$$S_x = (S_x^i)_{i \in [1, \ldots z]}$$

$$S_y = (S_y^i)_{i \in [1, \ldots z]}$$

$$S_z = (S_z^i)_{i \in [1, \ldots z]}$$

Likewise, the barometer 8 is configured to deliver z atmospheric pressure samples per window:
$P^i[n]$ is the i-th pressure sample delivered by the barometer (8) within time window n,
$\overline{P}[n]$ is the average pressure within time window n.

For convenience, in the rest of the description, the following notation will be used: $P = (P^i)_{i \in [1, \ldots z]}$.

The proposed method relies on a machine learning approach based upon the hypothesis that the step length $\widehat{SL}$ may be computed using a function, denoted g, of a set of M gait features $F_1, F_2, \ldots, F_M$ (M being an integer):

$$\widehat{SL} = g(F_1, F_2, \ldots, F_m).$$

Six gait features (M=6) are considered here, five of which are computed from the acceleration measures $S_x$, $S_y$, $S_z$ delivered by the accelerometer 7, and one of which is computed from the atmospheric pressure measures P delivered by the barometer 8.

$F_1[n]$ is an estimated gait cadence of the individual over time window n: $F_1[n] = \widehat{cad}[n]$. In one preferred embodiment, feature $F_1[n] = \widehat{cad}[n]$ is estimated from a known algorithm proposed by Fasel (op. cit. pp. 1775-1778). More precisely, feature $F_1[n]$ over time window n is computed by the steps of:

computing the norms of the acceleration measures ($S_x[n]$, $S_y[n]$, $S_z[n]$)=$(S_x^i[n], S_y^i[n], S_z^i[n])_{i \in [1, \ldots z]}$ delivered by the accelerometer 7, applying a Fast Fourier Transform to such computed acceleration norm, applying a Comb filter to such Fast Fourier Transform, resulting in a cadence likelihood function, attributing the maximum value of the likelihood function in the range of frequencies below 2 Hz to $F_1[n]=\widehat{cad}[n]$.

$F_2[n]$ is an estimated slope A of the path 4. It is assumed that the step length SL decreases uphill (where slope A is positive, FIG. 4) and increases downhill (where slope A is negative, FIG. 5). In one preferred embodiment, feature $F_2[n]$ over time window n is computed from the atmospheric pressure measures P[n] delivered by the barometer 8. More precisely, a line is fitted to –P[n] using a least square method, and the slope of this line is extracted as the slope of feature $F_2[n]$. In other words, $F_2[n]=A\equiv-P[n]$ where the symbol $\equiv$ represents correspondence between A and the linear coefficient of the regression line fitting the variations of –P[n]. This is reflected by the following equation:

$$F_2[n] = -\frac{\sum_{i=1}^{z}(i-\bar{\imath})(P^i[n]-\overline{P}[n])}{\sum_{i=1}^{z}(i-\bar{\imath})^2},$$

where $\bar{\imath}$ is computed as follows:

$$\bar{\imath} = \frac{1}{z}\sum_{i=1}^{z} i.$$

$F_3[n]$ is an estimated energy of the acceleration measures $S_y$ along the Y axis, over time window n. It is assumed there is a neural coupling between the arms and feet movements during gait. Indeed, when the individual increases his step length, the range of arm movement is increased, which leads to an increase in the energy of the acceleration measures $S_y$ along the Y axis (the one aligned with the wrist). In one preferred embodiment, feature $F_3[n]$ is computed as the standard deviation of acceleration $S_y$ over time window n:

$F_3[n]=\text{std}(S_y[n])$, that is to say $F_3[n]=\text{std}(S_y^i[n])_{i \in [1, \ldots z]}$.

$F_4[n]$ is an estimated mean absolute jerk of wrist acceleration over time window n. During gait periods, especially running, regular impacts are witnessed on the wrist 2 from variations of accelerations, the frequency of which is equal to the step frequency. The mean absolute value of jerk (i.e. the differential of acceleration) provides information about the energy of such impacts. In one preferred embodiment, feature $F_4[n]$ is computed as the mean of the differential of the acceleration measures $S_y$ along the Y axis:

$F_4[n]=\text{mean}(|S_y^i[n]-S_y^{i-1}[n]|)_{i \in [1, \ldots z]}$.

$F_5[n]$ is an estimated energy of wrist swing over time window n. It is an estimation of energy of the acceleration measures $S_x$ along X axis and $S_z$ along Z axis. When the step length is increased during walking, the wrist swing increases, thereby increasing its energy. Feature $F_5[n]$ of wrist swing is computed through the following equation, which provides the standard deviation of acceleration norm of $S_x$ along the X axis and $S_z$ along the Z axis:

$F_5[n]=\text{std}(\sqrt{S_x[n]^2+S_z[n]^2})$, that is to say $F_5[n]=\text{std}(\sqrt{S_x^i[n]^2+S_z^i[n]^2})_{i \in [1, \ldots z]}$.

$F_6[n]$ is an estimated mean of acceleration norm over time window n. During walking, the wrist 2 oscillates around the trunk while the body is moving forward. Feature $F_6[n]$, which denotes a degree of the body movement, is computed as follows:

$F_6[n]=\text{mean}(\sqrt{S_x[n]^2+S_y[n]^2+S_z[n]^2})$, that is to say $F_6[n]=\text{mean}(\sqrt{S_x^i[n]^2+S_y^i[n]^2+S_z^i[n]^2})_{i \in [1, \ldots z]}$.

The fact that the natures of the movement of wrist 2 during walking and running are different has been taken into consideration. For instant, during walking, the wrist 2 follows a pendulum swing movement that is absent in running.

In order to better fit the model to the type of gait, different combinations of features $F_1, F_2, \ldots, F_6$ are used to implement the method in running and walking, respectively.

More precisely, while $F_1, F_2, F_3, F_4$ are used for computing function g in a running situation, $F_1, F_2, F_4, F_5, F_6$ are used for computing said function in a walking situation.

The method for computing the step length $\widehat{SL}$ includes two procedures, namely:

a personalization procedure, including:
 an offline training phase 100 based upon GNSS data and that is conducted only once at the beginning of the path 4, and
 an online training phase 200 which is initiated through the results provided by the offline training phase and which is repeated along the path 4, an estimation procedure 300.

Personalisation Procedure

Under the personalisation procedure, the GNSS transponder 9 is ON and delivers instant speeds of the smartwatch 3.

Offline training phase

The offline training phase 100 is conducted over an initial time window 0 that does not represent the beginning of the running or walking session but a few seconds later. The offline training phase 100 aims at building an initial model to estimate the step length and the speed of the individual, and includes the steps of:

i) Measuring 102 an initial speed V[0] by the GNSS transponder 9 over the initial time window 0.

ii) Computing 104 an initial step cadence $\widehat{cad}[0]$ from acceleration measures $S_x[0]$, $S_y[0]$, $S_z[0]$ delivered by the accelerometer 7 over the initial time window 0.

Initial step cadence $\widehat{cad}[0]$ is computed using the steps to compute feature $F_1[n]$, wherein n=0 ($\widehat{cad}[0]=F_1[0]$).

iii) Computing 106 an initial step length SL[0] from the initial speed V[0] and the initial step cadence $\widehat{cad}[0]$.

The initial step length SL[0] is inferred from the initial speed V[0] and the initial step cadence $\widehat{cad}[0]$ according to the following equation:

$$SL[0] = \frac{V[0]}{\widehat{cad}[0]}.$$

iv) Computing 108 an initial vector of features X[0] from the acceleration measures $S_x[0]$, $S_y[0]$, $S_z[0]$ and the atmospheric pressure P[0] over the initial time window 0.

The initial vector of features X[0] is computed as follows:
For running:

$$X[0]=[1\ F_1[0]\ F_2[0]\ F_3[0]\ F_4[0]F_2^2[0]],$$

For walking:

$$X[0]=[1\ F_1[0]\ F_2[0]\ F_4[0]\ F_5[0]F_6[0]].$$

$F_1[0]$, $F_2[0]$, $F_3[0]$, $F_4[0]$, $F_5[0]$ and $F_6[0]$ are computed using the steps to compute $F_1[n]$, $F_2[n]$, $F_3[n]$, $F_4[n]$, $F_5[n]$ and $F_6[n]$, wherein n=0.

v) Computing 110 an initial coefficient vector β[0] from the initial vector of features X[0] and the initial step length S L[0], following a least square method.

The initial coefficient vector β[0] is computed from the initial vector of features X[0] and the initial step length SL[0]:

$$\beta[0]=(X[0]^TX[0])^{-1}X[0]^TSL[0],$$

where $(X[0]^TX[0])^{-1}$ is called initial dispersion matrix and is also noted D[0] in a simplified notation.

The previous equation may therefore be written as follows:

$$\beta[0]=D[0]X[0]^TSL[0].$$

β[0], X[0], D[0], SL[0], V[0] and $\widehat{cad}$ [0] are referred to as initial parameters. Online training phase The online training phase 200 is performed once the offline training phase 100 is over. The online training phase 200 aims at personalizing the initial model built during the offline training phase 100, and comprises the following steps, sporadically repeated for several time windows n:

i) Measuring 202 an instant speed V[n] by the GNSS transponder 9 over time window n.

ii) Computing 204 an instant cadence $\widehat{cad}$ [n] from the acceleration measures $S_x[n]$, $S_y[n]$, $S_z[n]$ delivered by the accelerometer 7 over time window n.

The instant step cadence $\widehat{cad}$ [n] is computed using the steps to compute feature $F_1$. As a reminder, $F_1[n]=\widehat{cad}$ [n].

iii) Computing 206 an instant step length SL[n] from the instant speed V[n] and the instant step cadence $\widehat{cad}$ [n]

$$SL[n]=\frac{V[n]}{\widehat{cad}[n]}$$

iv) Computing 208 an instant vector of features X[n] from the acceleration measures $S_x[n]$, $S_y[n]$, $S_z[n]$ delivered by the accelerometer 7 and atmospheric pressure measures P[n] delivered by the barometer 8 over time window n.

The instant vector of feature X[n] is computed as follows:
For running:

$$X[n]=[1\ F_1[n]\ F_2[n]\ F_3[n]\ F_4[n]F_2[n]^2],$$

For walking:

$$X[n]=[1\ F_1[n]\ F_2[n]\ F_4[n]\ F_5[n]F_6[n]].$$

v) Computing 210 an instant coefficient vector β[n] from the preceding coefficient vector β[n-1] following a recursive least square method.

The instant coefficient vector [n] is computed as follows:

$$\beta[n]=\beta[n-1]+D[n]X[n](SL[n]-X[n]^T\beta[n-1]),$$

where D[n] is a dispersion matrix defined (in theory) by $D[n]=(X[n]^TX[n])^{-1}$. However, to simplify calculation and hence limit memory space, the dispersion matrix D[n] is computed according to the following recursive equation:

$$D[n]=D[n-1](I-X[n](I+X[n]^TD[n-1]X[n])^{-1}X[n]^T D[n-1]),$$

where I denotes the identity matrix.

The recursive computing of equation for computing β[n] starts from β[1]:

$$\beta[1]=\beta[0]+D[1]X[1](SL[1]-X[1]^T\beta[0]),$$

where D[1] is computed using equation for computing D[n] in which the initial dispersion matrix $D[0]=(X[0]^TX[0])^{-1}$ is injected:

$$D[1]=D[0](I-X[1](I+X[1]^TD[0]X[1])^{-1}X[1]^TD[0]).$$

Estimation Procedure

Under the estimation procedure 300, the GNSS transponder 9 is OFF. The estimation procedure aims at estimating the speed, cadence and step length of the individual using only the inertial sensors.

The estimation procedure 300 includes the following steps, for an arbitrary time window n', n' ∈ [1, . . . , N]:

i) Computing 302 an instant vector of features X[n'] from the acceleration measures $S_x[n']$, $S_y[n']$, $S_z[n']$ delivered by the accelerometer 7 and atmospheric pressure measures P[n'] delivered by the barometer 8 over time window n'.

ii) Computing 304 an instant step length $\widehat{SL}$ [n'] from the instant vector of features X[n'] and the most updated coefficient vector β[n], using the following formula:

$$\widehat{SL}\ [n']=X[n']\beta[n].$$

iii) Computing 306 an instant cadence $\widehat{cad}$ [n'] from the acceleration measures $S_x[n']$, $S_y[n']$, $S_z[n']$ delivered by the accelerometer 7 over time window n'.

iv) Computing 308 an instant speed $\hat{V}[n']$ from the instant step length $\widehat{SL}$ [n'] and the instant cadence $\widehat{cad}$ [n'], using the following formula:

$$\hat{V}[n]=\widehat{SL}\ [n']\times \widehat{cad}\ [n'].$$

This method provides an acceptable memory consumption cost and is capable of providing real-time computing of the step length $\widehat{SL}$ [n'] and the speed $\hat{V}[n']$ over a time window n'. The use of the disclosed recursive least square method for computing the coefficient vectors provides good results without the need of all previous computed data.

Indeed, the method was tested on thirty healthy active volunteers who participated to a 90 minutes outdoor walking and running on a path having various terrain conditions including flat, uphill and downhill.

Figure 9:
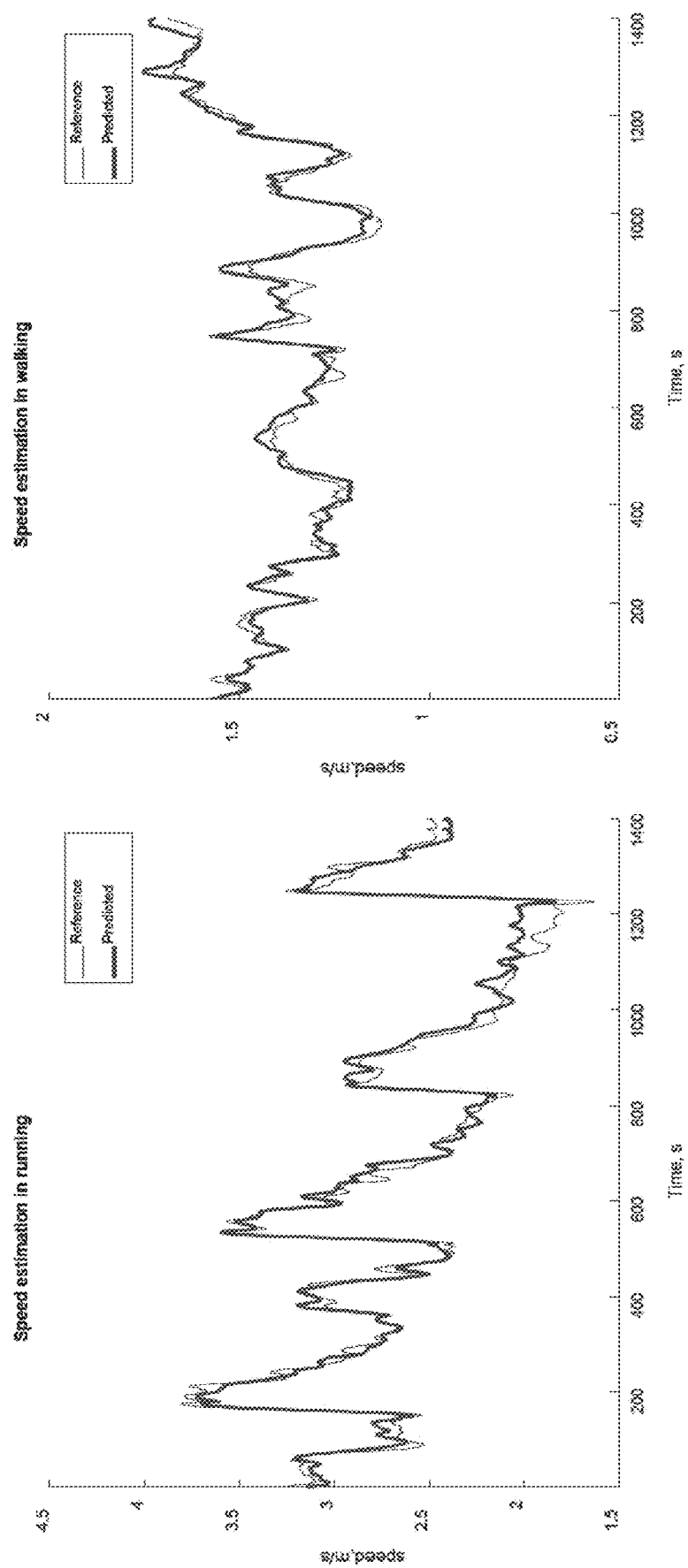
FIG. 9 is a diagram showing two pairs of superposed curves: on the left, a pair of superposed speed curves of a running individual, including a GNSS-built reference curve, and a prediction curve computed with the method of the invention; on the right, the same for a walking individual.

FIG. 9 shows that the computed speed (in bold line) is close to the actual one (measured through a GNSS, in thin line), whichever the gait (running, on the left; walking, on the right).

This method is inherently user-dependent and hence personalized to each individual. It provides an online learning process where the step length and speed are inferred from instant inputs and from previous computations using a recursive least square model.

The tests conducted on volunteers showed that the error gradually decreases along the path. It proves to have low power consumption, high accuracy, practicality (the method is implemented in a wrist-wearable device) and good ergonomics (no need to calibrate sensors). This method is suitable for a daily use on a long-term basis.

The invention claimed is:

1. A method for computing an estimation of a step length $\widehat{SL}$ [n'] of an individual running along a path, over a time window n', n' being an integer higher than or equal to 1,
said individual being equipped with a wrist-wearable device comprising:
a calculation circuit,
a GNSS transponder configured to deliver instant speeds of the wrist-wearable device,
a barometer configured to deliver instant atmospheric pressure measures (P),
an accelerometer configured to deliver instant acceleration measures along three perpendicular axes, namely:
a first acceleration $S_x$ along an X axis perpendicular to a wrist and parallel to a sagittal plane (P1) of the individual;
a second acceleration $S_y$ along a Y axis parallel to the wrist and parallel to the sagittal plane (P1) of the individual;
a third acceleration $S_z$ along a Z axis perpendicular to the wrist and parallel to a front plane (P2) of the individual;
said method comprising the following steps, carried out by the calculation circuit:
computing a vector of features X[n] over a time window n, n being an integer higher than or equal to 1, as follows:

$$X[n]=[1\ F_1[n]\ F_2[n]\ F_3[n]\ F_4[n]\ F_2^2[n]]$$

where:
feature $F_1[n]$ is an instant cadence $\widehat{cad}$ [n'] of the individual over time window n, computed from norms of the instant acceleration measures $S_x[n], S_y[n], S_z[n]$ delivered by the accelerometer over time window n,
feature $F_2[n]$ is an instant slope of the path computed from the instant atmospheric pressure measures (P[n]) delivered by the barometer over time window n,
feature $F_3[n]$ is an instant energy of the second acceleration measures $S_y[n]$ delivered by the accelerometer over time window n, and
feature $F_4[n]$ is an instant mean absolute jerk of the second acceleration measures $S_y[n]$ delivered by the accelerometer over time window n, and
computing a coefficient vector β[n] over time window n as follows:

$$β[n]=β[n-1]+D[n]X[n](SL[n]-X[n]^Tβ[n-1])$$

where:
D[n] is a dispersion matrix of the instant vector of features X[n], $$SL[n] = \frac{V[n]}{\widehat{cad}[n]},$$

V[n] is a speed of the wrist-wearable device, measured by the GNSS transponder over time window n,
β[0] is an initial parameter,
computing a vector of features X[n'] over time window n', as follows:

$$X[n']=[1\ F_1[n']\ F_2[n']\ F_3[n']\ F_4[n']\ F_2^2[n']],\ \text{and}$$

computing the step length $\widehat{SL}$ [n'] as follows:

$$\widehat{SL}\ [n']=X[n']β[n].$$

2. The method according to claim 1, wherein feature $F_1$ [n] is computed by the steps of:
computing the norms of the acceleration measures $(S_x^i[n]\ S_y^i[n]\ S_z^i[n])_{i∈[1,\ldots,z]}$ delivered by the accelerometer,
applying a Fast Fourier Transform to the computed acceleration norms,
applying a Comb filter to such Fast Fourier Transform, resulting in a cadence likelihood function, and
attributing the maximum value of the likelihood function in the range of frequencies below 2 Hz to $F_1[n]$.

3. The method according to claim 1, wherein feature $F_2$ [n] is computed as follows:

$$F_2[n] = -\frac{\sum_{i=1}^{z}(i-\bar{i})(P^i[n]-\bar{P}[n])}{\sum_{i=1}^{z}(i-\bar{i})^2},$$

where:
$P^i$ [n] is the i-th pressure sample delivered by the barometer within time window k,
$\bar{P}[n]$ is the average pressure within time window n, and
$\bar{i}$ is computed as follows:

$$\bar{i} = \frac{1}{z}\sum_{i=1}^{z} i$$

where z is number of samples within time window n.

4. The method according to claim 1, wherein feature $F_3$ [n] is computed as the standard deviation of second acceleration measures $S_y[n]$:

$$F_3[n]=\text{std}(S_y[n]).$$

5. The method according to claim 1, wherein feature $F_4$ [n] is computed as follows:

$$F_4[n]=\text{mean}(|S_y^i[n]-S_y^{i-1}[n]|)$$

where $S_y^i$ [n] is the i-th acceleration sample along the Y axis, delivered by the accelerometer within time window n.

6. The method according to claim 1, wherein D [n] is computed as follows:

$$D[n]=D[n-1](1-X[n]+X[n]^TD[n-1]X[n])^{-1}X[n]^TD[n-1]),$$

where $$D[0]=(X[0]^TX[0])^{-1},\ \text{and}$$

X[0] is an initial parameter.

7. The method for calculating an estimation of the speed $\hat{V}$[n'] of an individual running or walking along a path, over a time window n', comprising:
computing the step length $\widehat{SL}$ [n'] of the individual according to the method of claim 1, and
calculating the speed $\hat{V}$[n'] using the following formula:

$$\hat{V}[n']=\widehat{SL}\ [n']\times \widehat{cad}\ [n'].$$

8. A computer program product implemented on a non-transitory computer readable medium containing computer instructions stored therein for causing a computer processor to perform the method according to claim 1.

9. A wrist-wearable device comprising a calculation circuit and a non-transitory computer readable medium connected to the calculation circuit, said non-transitory computer medium containing computer instructions store therein according to claim 8.

10. A method for computing an estimation of the step length $\widehat{SL}[n']$ of an individual walking along a path, over a time window n', n' being an integer higher than or equal to 1, said individual being equipped with a wrist-wearable device comprising:
a calculation circuit,
a GNSS transponder configured to deliver instant speeds of the device,
a barometer configured to deliver instant atmospheric pressure measures (P),
an accelerometer configured to deliver instant acceleration measures along three perpendicular axes, namely:
a first acceleration $S_X$ along an X axis perpendicular to a wrist and parallel to a sagittal plane (P1) of the individual;
a second acceleration $S_y$ along a Y axis parallel to the wrist and parallel to the sagittal plane (P1) of the individual;
a third acceleration $S_Z$ along a Z axis perpendicular to the wrist and parallel to a front plane (P2) of the individual;
said method comprising the following steps, carried out by the calculation circuit:
computing a vector of features X[n] over a time window n, n being an integer higher than or equal to 1 as follows:

$$X[n]=[1\,F_1[n]\,F_2[n]\,F_4[n]\,F_5[n]\,F_6[n]]$$

where:
feature $F_1[n]$ is an instant cadence $\widehat{cad}[n']$ of the individual over time window n, computed from the norms of the instant acceleration measures $S_x[n]$, $S_y[n]$, $S_z[n]$ delivered by the accelerometer over time window n,
feature $F_2[n]$ is an instant slope of the path computed from the instant atmospheric pressure measures (P[n]) delivered by the barometer over time window n,
feature $F_4[n]$ is an instant mean absolute jerk of the second acceleration measures $S_y[n]$ delivered by the accelerometer over time window n,
feature $F_5[n]$ is an estimation of energy of the acceleration measures Sx along X axis and Sz along Z axis over time windows n, and
feature $F_6[n]$ is an estimated mean of acceleration norm over time window n, computing a coefficient vector β[n] over time window n as follows:

$$\beta[n]=\beta[n-1]+D[n]X[n](SL[n]-X[n]^T\beta[n-1])$$

where:
D[n] is [[the]] a dispersion matrix of the instant vector of features X [n], $$SL[n] = \frac{V[n]}{\widehat{cad}[n]},$$

V[n] is a speed of the wrist-wearable device, measured by the GNSS transponder over time window n, and
β[0] is an initial parameter,
computing a vector of features X[n'] over time window n', as follows:

$$X[n']=[1\,F_1[n']\,F_2[n']\,F_4[n']\,F_5[n']\,F_6[n']],\text{ and}$$

computing the step length $\widehat{SL}[n']$ as follows:

$$\widehat{SL}[n']=X[n']\beta[n].$$

11. The method according to claim 10, wherein feature $F_5[n]$ is computed as follows:

$$F_5[n]=\text{std}(\sqrt{S_x^2[n]+S_z^2[n]^2}).$$

12. The method according to claim 10, wherein the instant mean $F_6[n]$ of acceleration norm is computed as follows:

$$F_6[n]=\text{mean}(\sqrt{S_x^2[n]+S_y^2[n]+S_z^2[n]}).$$

\* \* \* \* \*